(12) United States Patent
Graham

(10) Patent No.: US 11,304,856 B2
(45) Date of Patent: Apr. 19, 2022

(54) INTERGLUTEAL SHIELD

(71) Applicant: Graham Tackle, LLC, Homestead, FL (US)

(72) Inventor: Michael Gregory Graham, Homestead, FL (US)

(*) Notice: Subject to any disclaimer, the term of this patent is extended or adjusted under 35 U.S.C. 154(b) by 702 days.

(21) Appl. No.: 16/212,496

(22) Filed: Dec. 6, 2018

(65) Prior Publication Data

US 2019/0175417 A1 Jun. 13, 2019

Related U.S. Application Data

(60) Provisional application No. 62/597,712, filed on Dec. 12, 2017.

(51) Int. Cl.
*A61F 13/15* (2006.01)
*A61F 13/45* (2006.01)
*A61F 13/531* (2006.01)

(52) U.S. Cl.
CPC ........ *A61F 13/15203* (2013.01); *A61F 13/45* (2013.01); *A61F 13/531* (2013.01); *A61F 2013/1513* (2013.01); *A61F 2013/15544* (2013.01)

(58) Field of Classification Search
CPC .. A61F 13/15203; A61F 13/45; A61F 13/531; A61F 13/8405; A61F 2013/1513; A61F 2013/15138; A61F 2013/15544; A61F 2013/15552; A61F 2013/8411
See application file for complete search history.

(56) References Cited

U.S. PATENT DOCUMENTS

| | | | | |
|---|---|---|---|---|
| 2,742,042 A * | 4/1956 | Flanders | ................ | A61F 13/15 604/364 |
| 4,182,335 A * | 1/1980 | Matrullo | ................ | A61F 5/4401 604/359 |
| 4,880,417 A * | 11/1989 | Yabrov | ................ | A61F 5/4401 604/355 |
| 4,892,532 A | 1/1990 | Boman | | |
| 4,923,454 A | 5/1990 | Seymour et al. | | |
| 4,935,022 A | 6/1990 | Lash et al. | | |
| 6,277,770 B1 | 8/2001 | Smith, III et al. | | |
| 6,430,630 B1 * | 8/2002 | Hung | ................ | G06F 13/32 710/22 |
| 6,521,087 B2 | 2/2003 | Hansen et al. | | |
| 6,676,645 B1 | 1/2004 | Bitterhof | | |
| 6,716,229 B2 * | 4/2004 | Toth | ................ | A61F 5/0093 604/385.01 |
| 6,780,201 B2 | 8/2004 | Sun et al. | | |
| 6,997,915 B2 * | 2/2006 | Gell | ................ | A61F 13/474 604/385.16 |
| 7,364,639 B2 | 4/2008 | Hu et al. | | |

(Continued)

OTHER PUBLICATIONS

Beguin A., et al., Improving diaper design to address incontinence associated dermatitis, BMC Geriatrics 10:86 (2010).

*Primary Examiner* — Catharine L Anderson
(74) *Attorney, Agent, or Firm* — Law Office of Jerry Joseph, PLC; Jerry Joseph

(57) ABSTRACT

An intergluteal shield being a crescent or heart shaped or other shaped pad having a soft fabric exterior and lacking any waterproof layers, the pad being sized to fit into the intergluteal space of a human keeping the location dry. The intergluteal shield can be used to alleviate diaper rash, Hexsel's hydrosis and other intergluteal irritations.

14 Claims, 11 Drawing Sheets

(56) References Cited

U.S. PATENT DOCUMENTS

| | | | |
|---|---|---|---|
| 8,062,277 B2* | 11/2011 | Fleming | ............ A61F 13/47209 |
| | | | 604/385.17 |
| 2008/0145443 A1 | 6/2008 | Langolf et al. | |
| 2011/0021104 A1 | 1/2011 | Lin et al. | |
| 2011/0092935 A1 | 4/2011 | Hann | |
| 2018/0064587 A1* | 3/2018 | St Hl | ...................... A61F 13/84 |

* cited by examiner

INTERGLUTEAL SHIELD

PRIOR RELATED APPLICATIONS

This application claims priority to U.S. Ser. No. 62/597,712, filed Dec. 12, 2017, and incorporated by reference in its entirety for all purposes.

FEDERALLY SPONSORED RESEARCH STATEMENT

Not applicable.

FIELD OF THE DISCLOSURE

The disclosure generally relates to devices and methods to prevent and/or mitigate diaper rash and other irritations that occur between the glutes of an individual.

BACKGROUND OF THE DISCLOSURE

Diaper rash is the most common dermatitis found in infancy. Prevalence has been variably reported from 4-35% in the first 2 years of life. However, because fewer than 10% of all diaper rashes are reported, the actual incidence of this condition is likely highly underestimated.

The precise etiology of most diaper rashes is not clearly defined. The rashes likely result from a combination of factors that includes wetness, friction, urine and feces, and the presence of microorganisms. Anatomically, this skin region features numerous folds and creases, which present a problem with regard to both efficient cleansing and control of the microenvironment.

The main irritants in this situation are fecal proteases and lipases, whose activity is increased greatly by elevated pH. An acidic skin surface is also essential for the maintenance of the normal microflora, which provides innate antimicrobial protection against invasion by pathogenic bacteria and yeasts. Fecal lipase and protease activity is also greatly increased by acceleration of gastrointestinal transit; this is the reason for the high incidence of irritant diaper dermatitis observed in babies who have had diarrhea in the previous 48 hours.

The wearing of diapers causes a significant increase in skin wetness and pH. Prolonged wetness leads to maceration (softening) of the stratum corneum, the outer, protective layer of the skin, which is associated with extensive disruption of intercellular lipid lamellae. A series of diaper studies conducted mainly in the late 1980s found a significant decrease in skin hydration following the introduction of diapers with a superabsorbent core. Recent studies confirm that this trend is ongoing. Weakening of its physical integrity makes the stratum corneum more susceptible to damage by (1) friction from the surface of the diaper and (2) local irritants.

The normal pH of the skin is between 4.5 and 5.5. When urea from the urine and stool mix, urease breaks down the urine, decreasing the hydrogen ion concentration (increasing pH). Elevated pH levels increase the hydration of the skin and make the skin more permeable.

Previously, ammonia was believed to be the primary cause of diaper dermatitis. Recent studies have disproved this, showing that when ammonia or urine is placed on the skin for 24-48 hours, no apparent skin damage occurs.

A series of studies has shown that the pH of cleansing products can change the microbiological spectrum of the skin. High soap pH values encourage propioni bacterial growth on skin, whereas synthetic detergents with a pH of 5.5 did not cause changes in the microflora. A study looked to explain the relationship between skin barrier function in 4-day-old infants and the occurrence of diaper dermatitis during the first month of life. The study concluded that early neonatal skin pH may predict the risk of diaper dermatitis during the first month of life. These results may be useful in devising strategies to prevent diaper dermatitis.

The etiology of diaper rash is discussed next:

Miliaria Obstruction of eccrine sweat glands when the stratum corneum becomes excessively hydrated and edematous is believed to cause miliaria.

Intertrigo Intertrigo occurs when wet skin, which is more fragile and has a higher coefficient of friction, becomes damaged from maceration and chafing.

Contact dermatitis Irritant contact dermatitis is most likely made up of some combination of intertrigo and miliaria. In addition, it has been shown to result from the irritating effects of mixing urine with feces. Urine in the presence of fecal urease becomes more alkaline due to the production of ammonia. This alkaline urine causes activation of fecal lipases, ureases, and proteases. These, in turn, irritate the skin directly and increase its permeability to other low molecular weight irritants.

Candidal diaper dermatitis Once the skin is compromised, secondary infection by *Candida albicans* is common. Between 40% and 75% of diaper rashes that last for more than 3 days are colonized with *C. albicans*. Candida has a fecal origin and is not an organism normally found on perineal skin. Amoxicillin was found to increase the colonization by *Candida* and worsens the diaper dermatitis.

A study by Ersoy-Evans et al. of 63 infants with diaper rash found that those with *Candida* infection (77.4% of the patients) had a significantly greater median number of previous diaper rash episodes than did those with noncandidal diaper rash.

Bacterial diaper dermatitis Bacteria may play a role in diaper dermatitis through reduction of fecal pH and the resultant activation of enzymes. Additionally, fecal microorganisms probably contribute to secondary infections when they occur. This is particularly evident with bullous impetigo in the diaper area, which causes bullae that are flaccid but sometimes tense due to *Staphylococcus aureus* infection, or a cellulitis due to cutaneous *Streptococci*, or even a folliculitis due to *S. aureus* infection.

Polymicrobial growth is documented in at least half of diaper rash cultures. *Staphylococcus* species are the most commonly grown organisms, followed by *Streptococcus* species and organisms from the family Enterobacteriaceae. Nearly 50% of isolates also contain anaerobes.

Granuloma gluteale *infantum* Granuloma gluteale *infantum* is a rare disorder. It is not very well understood, but it probably represents an unusual inflammatory response to long-standing irritation, candidiasis, or fluorinated corticosteroids.

Treatment of diaper rash includes a combination of measures, which are most effective when used together. The letters ABCDE are a useful way to remember all of these measures:

A=air out the skin by allowing the child to go diaper-free
B=barrier; use a paste or ointment to protect the skin
C=clean; keep the skin clean
D=disposable diapers; during an episode of diaper rash, consider using disposable rather than cloth diapers
E=educate; educate yourself about how to prevent a recurrence of diaper rash Diaper-free periods The most effective way to treat irritant diaper rash is to reduce skin contact with urine and feces (i.e., by discontinuing or limiting the use of diapers). One way to do this is to allow the child to periodically go without a diaper, allowing the skin to be exposed directly to the air. Using a waterproof barrier under the child can minimize soiling. When the child wears a diaper, frequent diaper changes are recommended; a suggested interval might be every two to three hours and immediately after every bowel movement.

Skin barrier ointments or pastes Skin ointments or pastes also can help to treat or prevent irritant diaper rash. The ointment or paste should be applied at every diaper change and can be covered with a thin layer of petroleum jelly to prevent sticking to the diaper. The ointment or paste should be long-lasting and should stick to irritated or broken areas of skin. It is not necessary to completely clean the ointment or paste off the skin at diaper changes.

Lotions and creams are not as effective as ointments or pastes and are not recommended. In addition, products that contain preservatives, fragrances, or other additives are not recommended because they may further irritate the skin. It is important to closely read the ingredient label of all diaper products. Most diaper products contain ingredients such as zinc oxide and petrolatum, which form a protective skin barrier against wetness; some also contain lanolin, paraffin, or dimethicone.

Powders Powders that contain talc or corn starch can reduce friction and moisture. However, powders are not generally recommended as a treatment for diaper rash because the child could accidentally inhale them, and the FDA recommends against their use.

Antifungal treatments An antifungal treatment may be prescribed if the child is diagnosed with a yeast infection. Antifungal treatments are available as a cream, ointment, or powder. The treatment is usually applied two or three times per day and can be applied beneath a barrier skin ointment or paste, until the rash is gone.

Steroid ointment If the baby's skin becomes severely inflamed, the healthcare provider may recommend a mild, over-the-counter steroid ointment such as 1% hydrocortisone. This can be applied in a thin layer to the irritated skin twice per day for no more than one week. More potent or adult-strength steroid ointments are not recommended without the advice of a clinician. Steroid creams are not recommended because ingredients in the cream can be irritating.

Antibiotics If the baby develops signs or symptoms of a skin infection, a healthcare provider may prescribe an antibiotic ointment or oral antibiotic. Over-the-counter antibiotic creams or ointments (sample brand names: Neosporin, Bacitracin) are not recommended because they contain ingredients such as neomycin and bacitracin, to which many children are allergic.

Although the above advice helps to mitigate periods of diaper rash, there is always room for improvement, and even modest improvements can be of tremendous benefit to the exhausted parents of a screaming infant. This application provides one such improvement that can be used alone or with any one or more of the above.

SUMMARY OF THE DISCLOSURE

In parenting a newborn through intense periods of pain, crying, and everyone's lack of sleep due to diaper rash, the inventor discovered a new way of keeping the intergluteal region dryer by creating a diaper rash shield, which separates the glutes and allows airflow therebetween, preventing continued growth of organisms and allowing the region to heal.

Generally speaking, the intergluteal shield comprises a non-allergic cloth or fiber barrier that separates the glutes, allowing this region to remain dry and thus negating the growth of fungus or bacteria. Further, the intergluteal shield can be combined with one or medicaments to maintain a natural slightly acidic pH, treat fungal or bacterial growth and alleviate pain and inflammation.

The shape should be such as to fit interglutteally—e.g., between the glutes and preferably taking up most of the space so as to separate the skin on each cheek and allow airflow therebetween. It should fit without wrinkles and with a small amount protruding for gripping by a human hand. One preferred shape is a crescent moon, sized and shaped so as to follow the intergluteal curve of a baby. Another shape is a heart shape, folded in half. However, many shapes are possible, preferably having an interior or convex curved portion sized and shaped to accommodate an infant bottom, and the size and shape otherwise being convenient for insertion and removal, e.g. a small tab protruding from between the glutes for gripping and removing the shield.

The tab portion is small, so as to not create a lot of bulk in the diaper or other underwear, yet allow gripping with fingers. In some embodiments, it can also be omitted, as the shield can be gripped directly, especially for an infant shield. However, a tab is preferred as convenient, and if non-absorbent it will also provide a dry surface for the user to grip. A suitable tab size is about $0.5$ inch$^2$–$10$ inch$^2$, preferably about 3 or 2 inch$^2$ or most preferred 1 inch$^2$. The size may be somewhat larger for an adult pad if desired, and smaller tabs are more suitable for infants. The tab can be a separate rectangle or such protruding from the rest of the shield (see 21 in FIG. 2 or 41-44in FIG. 4), or the size and shape or curvature of the shield can be designed such that a portion will naturally protrude (e.g., the top of the heart 33 in FIG. 3 protrudes from the intergluteal space, as do the corners of a rectangle).

The shield is used between the glutes and can be changed with every diaper during periods of irritation. The shield allows air flow, and thus allows this region to stay dry, mitigating the irritating effect of constant wetness.

Although developed in response to a crying infant, we have since provided prototypes of the invention to adults with success. Adults can use an intergluteal shield in the event of severe diarrhea, when bedridden, or if suffering from Hexsel's hyperhidrosis (inguinal hyperhidrosis). Thus, the intergluteal shield can be available in a range of sizes to fit infants, children, and small or large adults.

The intergluteal shields can be disposable or reusable, as desired, and can be made with materials typically used to make diapers or breast milk shields, excepting the waterproof covers, which are not needed and indeed are contraindicated. The materials should be non-antigenic, non-irritating, non-toxic and completely baby safe. Preferred materials are organic, chlorine-free, perfume-free, dye-free, latex-free, and at least partially biodegradable, and use as little plastic as possible.

Some amount of surface texture may be preferred as proving softness and allowing airflow. Thus, fleeces, terrycloths, velvets, flannels and the like may be desirable. Alternatively, a non-woven stay-dry fabric can be used over a loose fiber fill. Non-woven synthetic materials are available with excellent wicking and stay-dry properties, and may be preferable, especially in disposable shields.

The central absorbent layer can be comprised of any absorbent material such as for example, cellulose, thermoplastic copolymers, cotton, or any of a number of the commonly available absorbent materials, including these materials containing or being impregnated with a gelling agent. The preferred central absorbent layer comprises cotton fibers and a gelling agent to cause any liquid entering the central absorbent layer to gel upon contact with the gelling agent.

Additional layers can be added to further improve dryness and wickability. A suitable inner wicking layer material is a thin hydrophobic material that is liquid permeable and thus allows fluid to wick through it to the central absorbent layer, while itself remaining dry and comfortable to the wearer. Such a material is disclosed in eg., U.S. Pat. Nos. 4,892,532 and 6,277,770, which are incorporated by reference herein in their entireties.

Without limitation, examples of suitable central absorbent layers include hydrophilic microfibers such as the hydrophilic nylon copolymer microfibers disclosed in U.S. Pat. No. 4,923,454, which is incorporated herein by this reference. A suitable gelling agent is a hydrogel-forming polymeric gelling agent such as hydrolyzed acrylonitrile grafted starch, polyacrylate grafted starch, polyacrylates, maleic anhydride-based copolymers, other substantially water-insoluble, slightly cross-linked, partially neutralized polymers, and combinations thereof, such as disclosed in U.S. Pat. No. 4,935,022, which is incorporated herein by this reference. Many such materials are known.

The layers can be adhered together, provided a non-allergenic adhesive is used and provided that care is taken to ensure soft edges. Any kind of welding can be used, depending on the materials such as heat welding, IR welding, ultrasound welding, and the like. The seams can also be stitched. In many cases, it may be preferred to invert the shield so that any seams or welds are on the inside, leaving a smooth soft exterior.

To use the shield, insert a first dry absorbent intergluteal shield into an intergluteal space of a human such that a portion of said intergluteal shield extends beyond said intergluteal space. Once the shield becomes damp or wet, grip that portion and remove the intergluteal shield, and replace with a second dry absorbent intergluteal shield into said intergluteal space. Continue as needed. Preferably, the shield is used with infants, but it is also suitable for use with adult humans.

The use of the word "a" or "an" when used in conjunction with the term "comprising" in the claims or the specification means one or more than one, unless the context dictates otherwise.

The term "about" means the stated value plus or minus the margin of error of measurement or plus or minus 10% if no method of measurement is indicated.

The use of the term "or" in the claims is used to mean "and/or" unless explicitly indicated to refer to alternatives only or if the alternatives are mutually exclusive.

The terms "comprise", "have", "include" and "contain" (and their variants) are open-ended linking verbs and allow the addition of other elements when used in a claim.

The phrase "consisting of" is closed, and excludes all additional elements.

The phrase "consisting essentially of" excludes additional material elements, but allows the inclusions of non-material elements that do not substantially change the nature of the invention, such as instructions for use, logos or designs, packaging, and the like.

BRIEF DESCRIPTION OF THE DRAWINGS

FIG. 1A shows a cover over an absorbent filler. FIG. 1B shows a two-layer shield made of terry cloth with the loops on the outside. FIG. 1C shows a two-layer velvet shield with the pile to the outside.

DETAILED DESCRIPTION

Figure 1A:
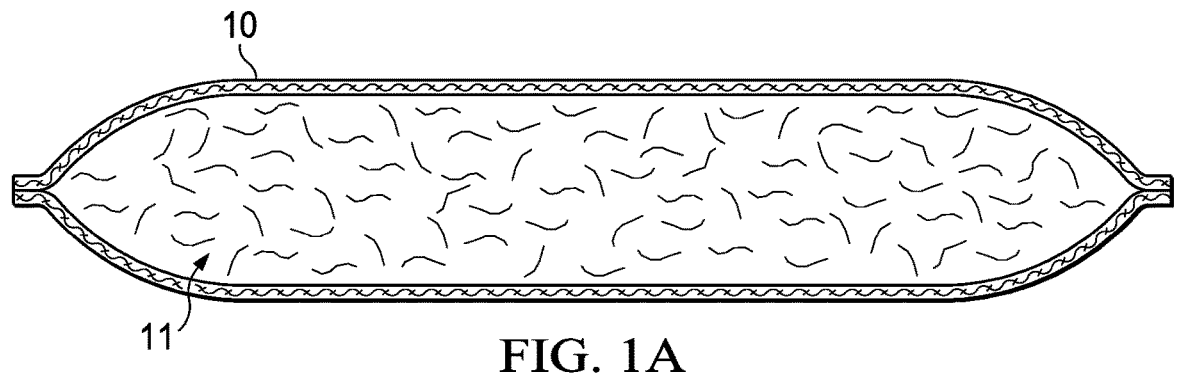
FIG. 1A-C. shows several embodiments in cross section.

FIG. 1. shows various embodiments of the intergluteal shield in cross section. In FIG. 1A, a cover 10 is shown over a loosely packed absorbent filler 11, and the edges can be welded, sewn or glued. The function of the filler is merely to provide adequate air flow, and thus the filler need not be absorbent, although it preferably is. Cover 10 can be any woven or non-woven fabric, and in some embodiments is preferably a "stay-dry" non-woven material, such as is common in diapers and breast milk shield. If desired, additional wicking layers can be added.

Figure 1B:
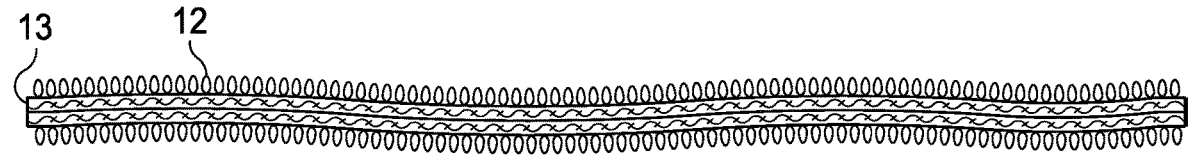
Figure 1C:
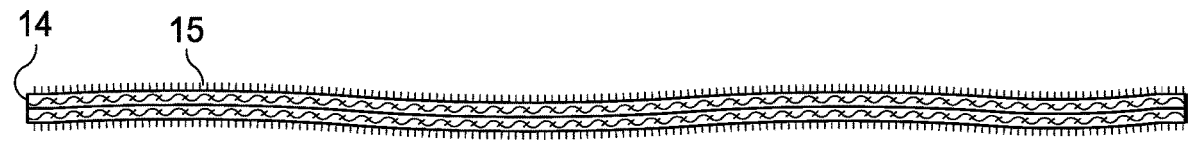

FIG. 1B shows a two-layer shield made of terry cloth fabric 13 with the loops 12 on the outside. FIG. 1C shows a two-layer velvet 14 shield, again with the pile 15 to the outside. These soft surfaces allow air flow and thus allow the intergluteal region to stay dry.

Figure 2:
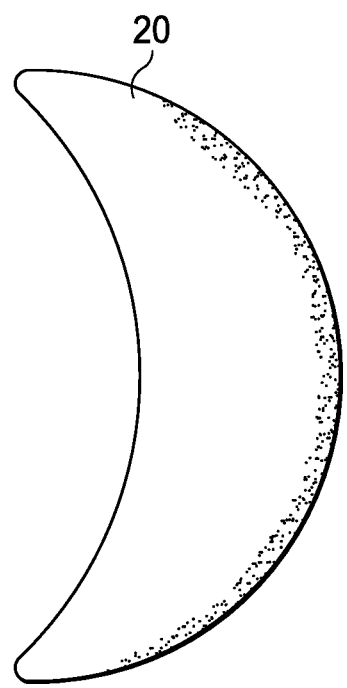
FIG. 2. shows a top plan view of a crescent moon shaped intergluteal shield.
Figure 3:
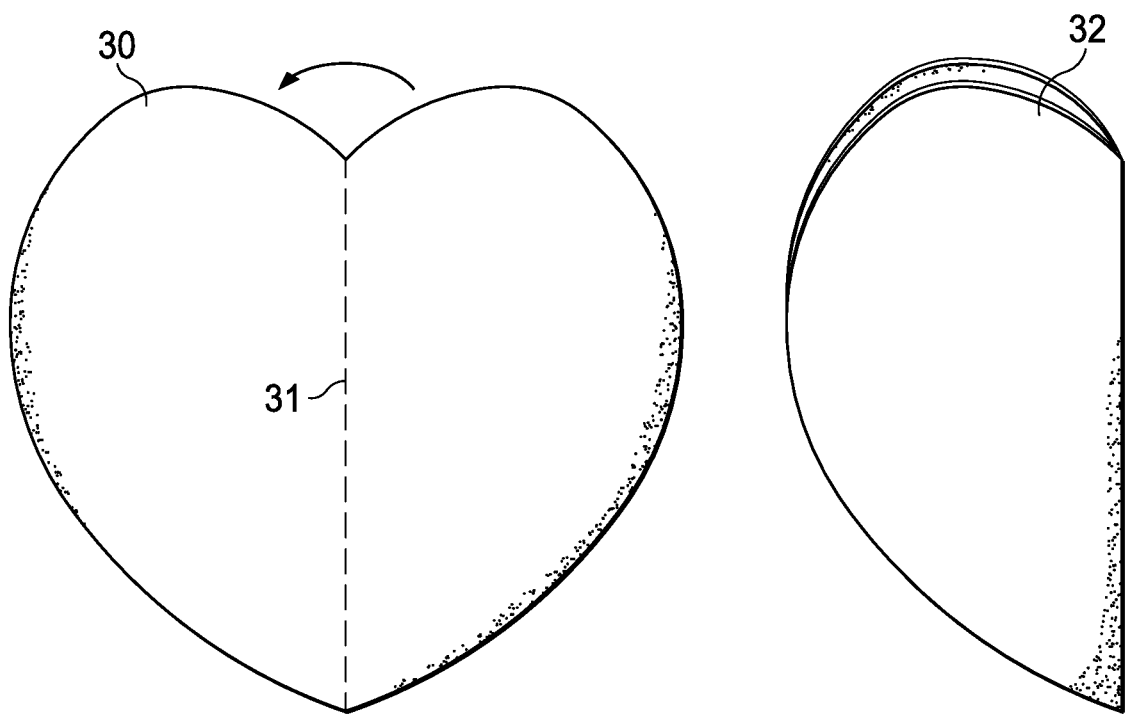
FIG. 3. shows a top plan view of a heart shaped intergluteal shield that is folded over for use.

FIG. 2. shows a top plan view of a crescent moon shaped intergluteal shield 20 with separate tab 21. FIG. 3 shows a top plan view of a heart shaped intergluteal shield 30 that is folded over for use. This embodiment may be particularly preferred as being very simple of manufacture, plus any edging material is away from the baby's skin during use. The fold is flat, rather than curved, thus the fit may suffer. However, a fabric with sufficient flex may provide good fit.

Figure 4:
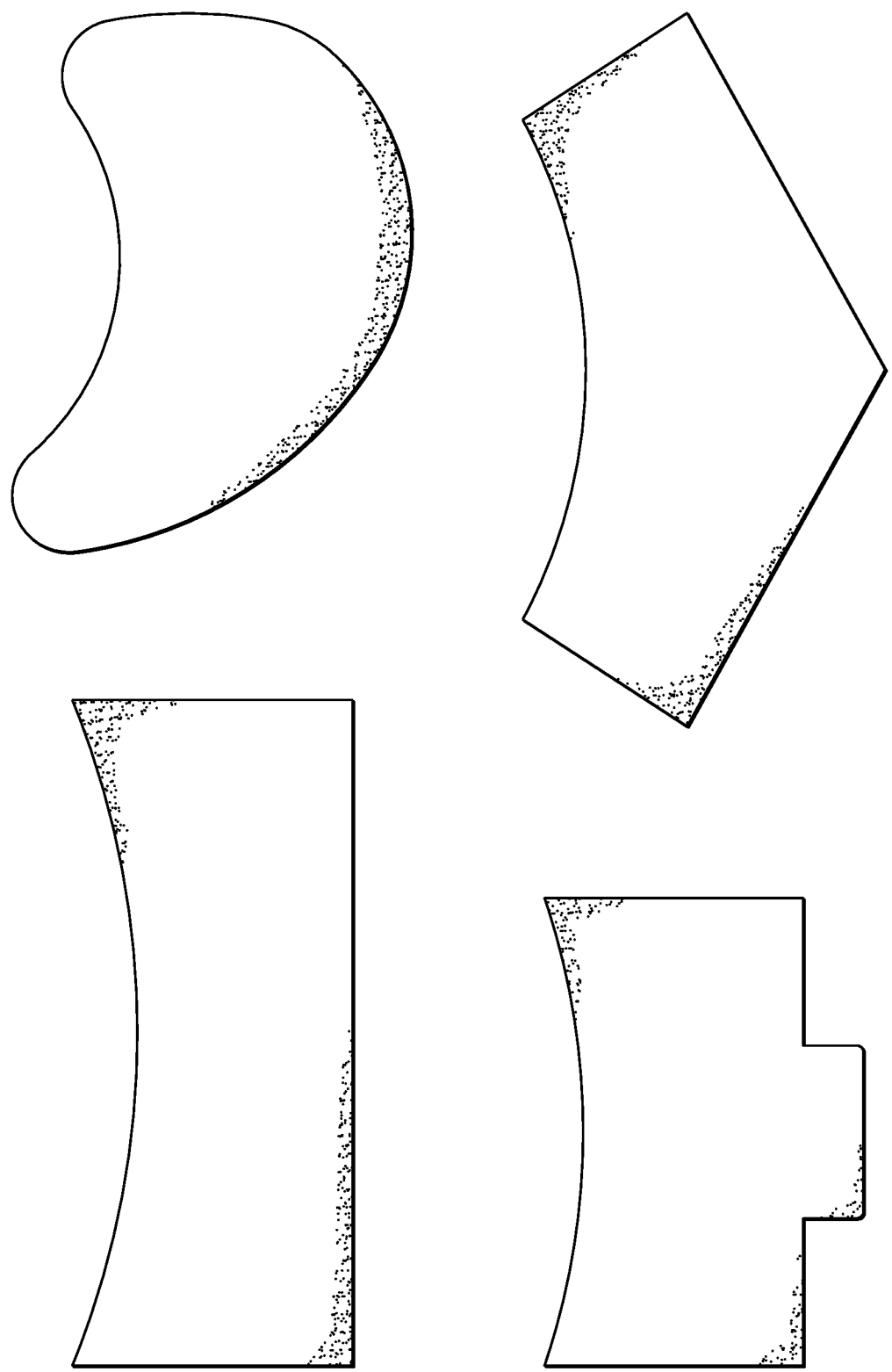
FIG. 4 shows a variety of shapes that could be used.
Figure 5:
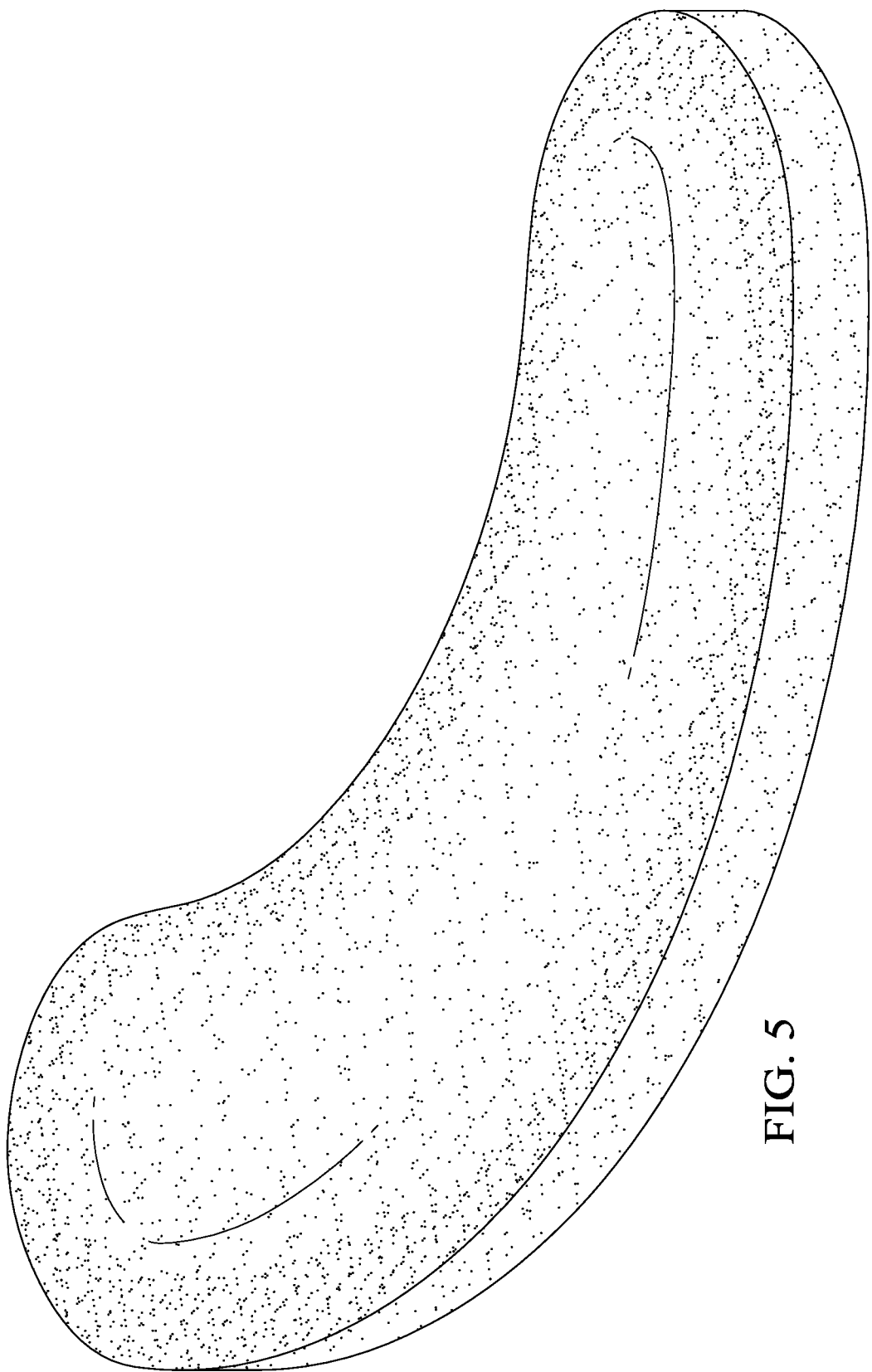
FIG. 5 is a top view of an un-embossed absorbent intergluteal shield according to one embodiment.
Figure 6:
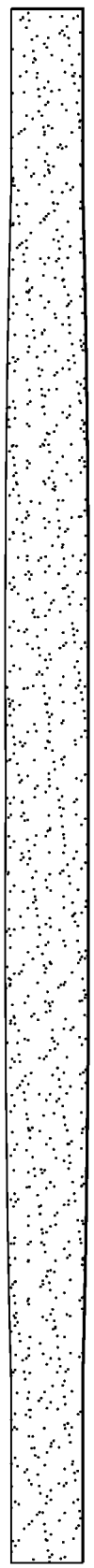
FIG. 6 is a side view of the shield of FIG. 5.
Figure 7:
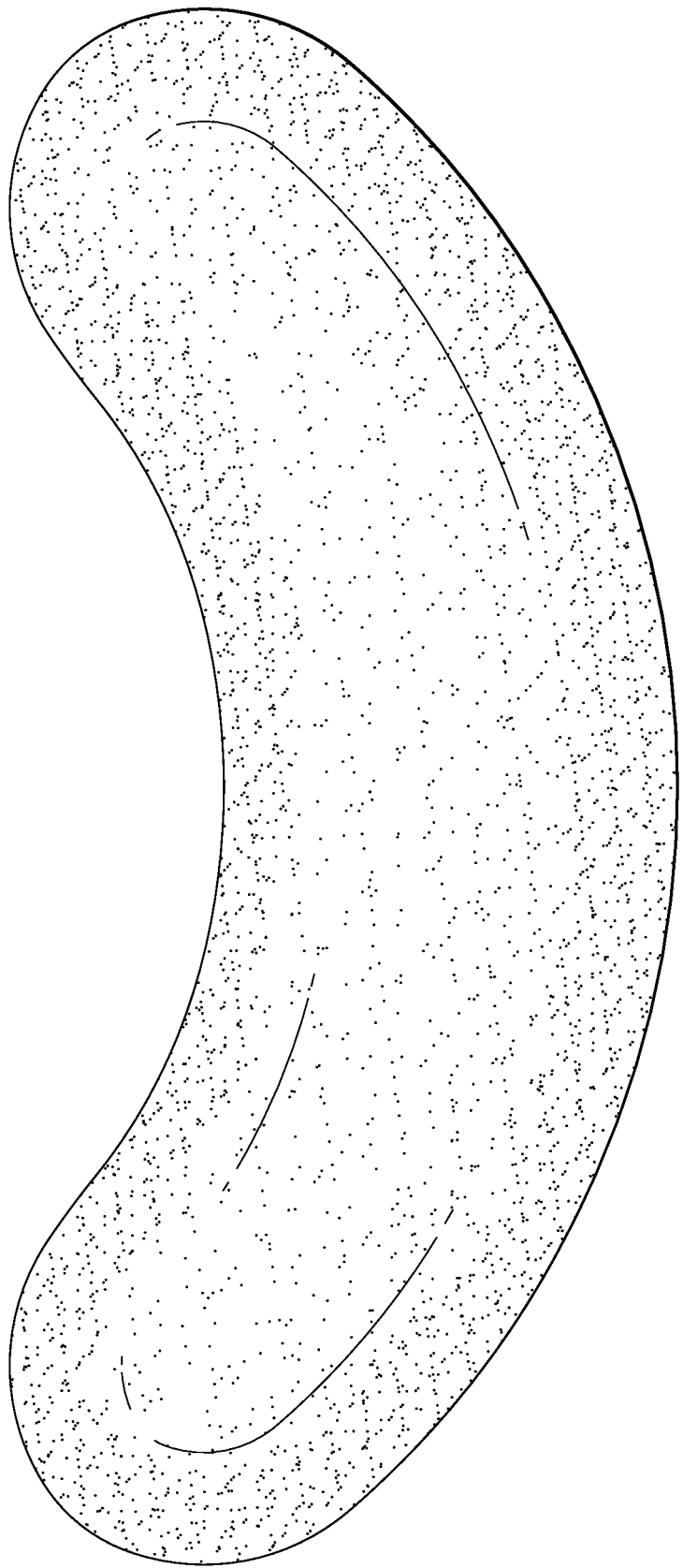
FIG. 7 is a top view of an un-embossed intergluteal shield according to another embodiment.
Figure 8:
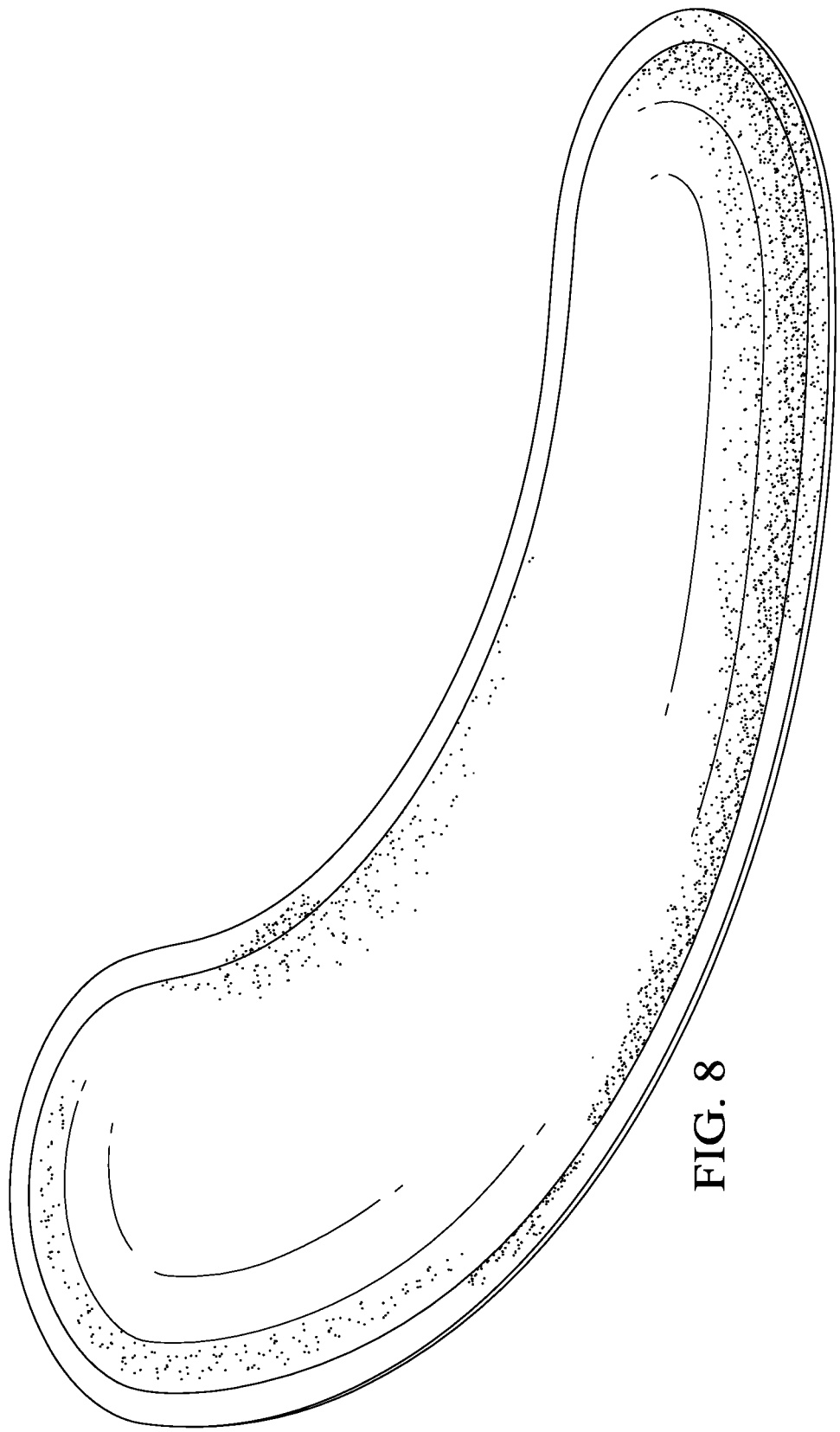
FIG. 8 is a top view of a shield having embossed edging around the periphery.
Figure 9:
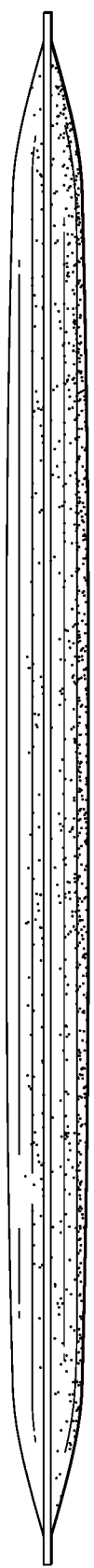
FIG. 9 is a side view of the shield of FIG. 8, where the edging is clearly visible.
Figure 10:
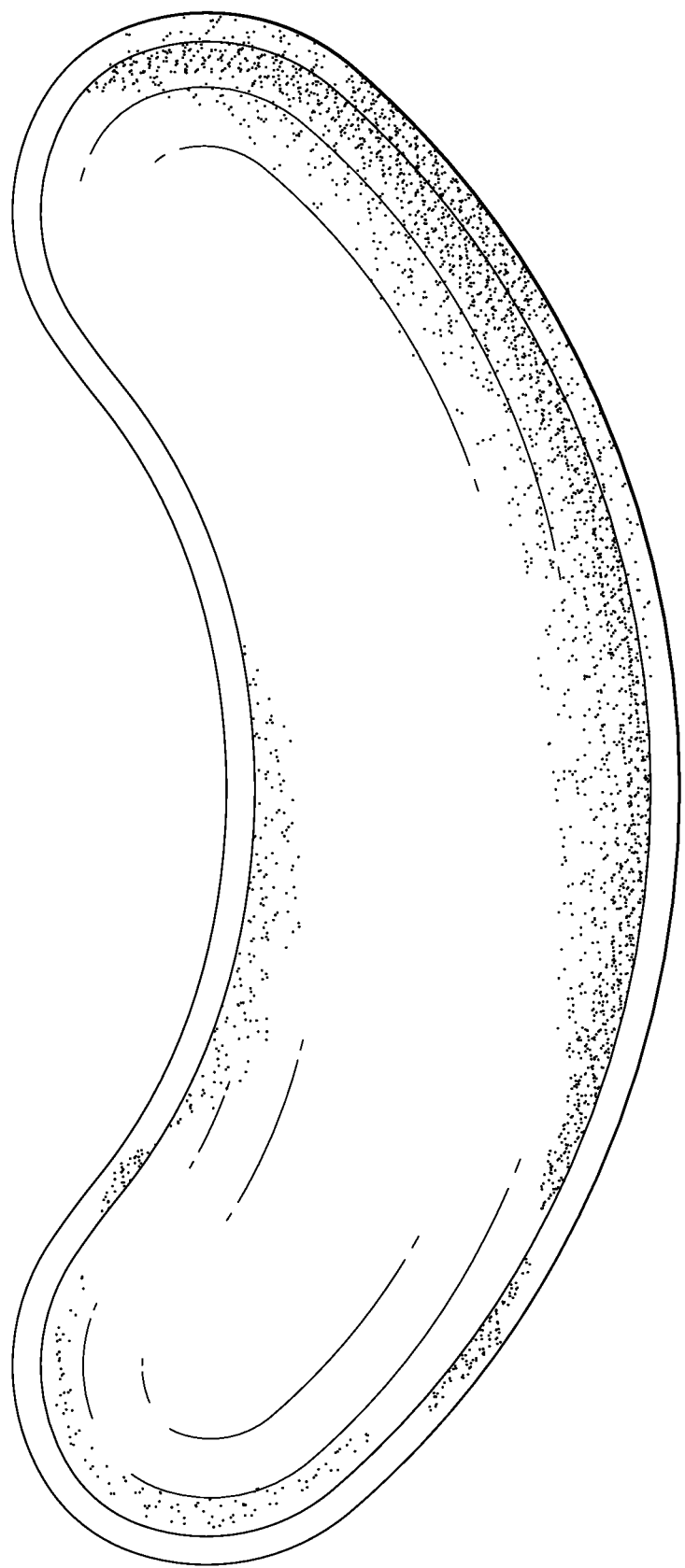
FIG. 10 is a top view of another shield having embossed edging around the periphery.
Figure 11:
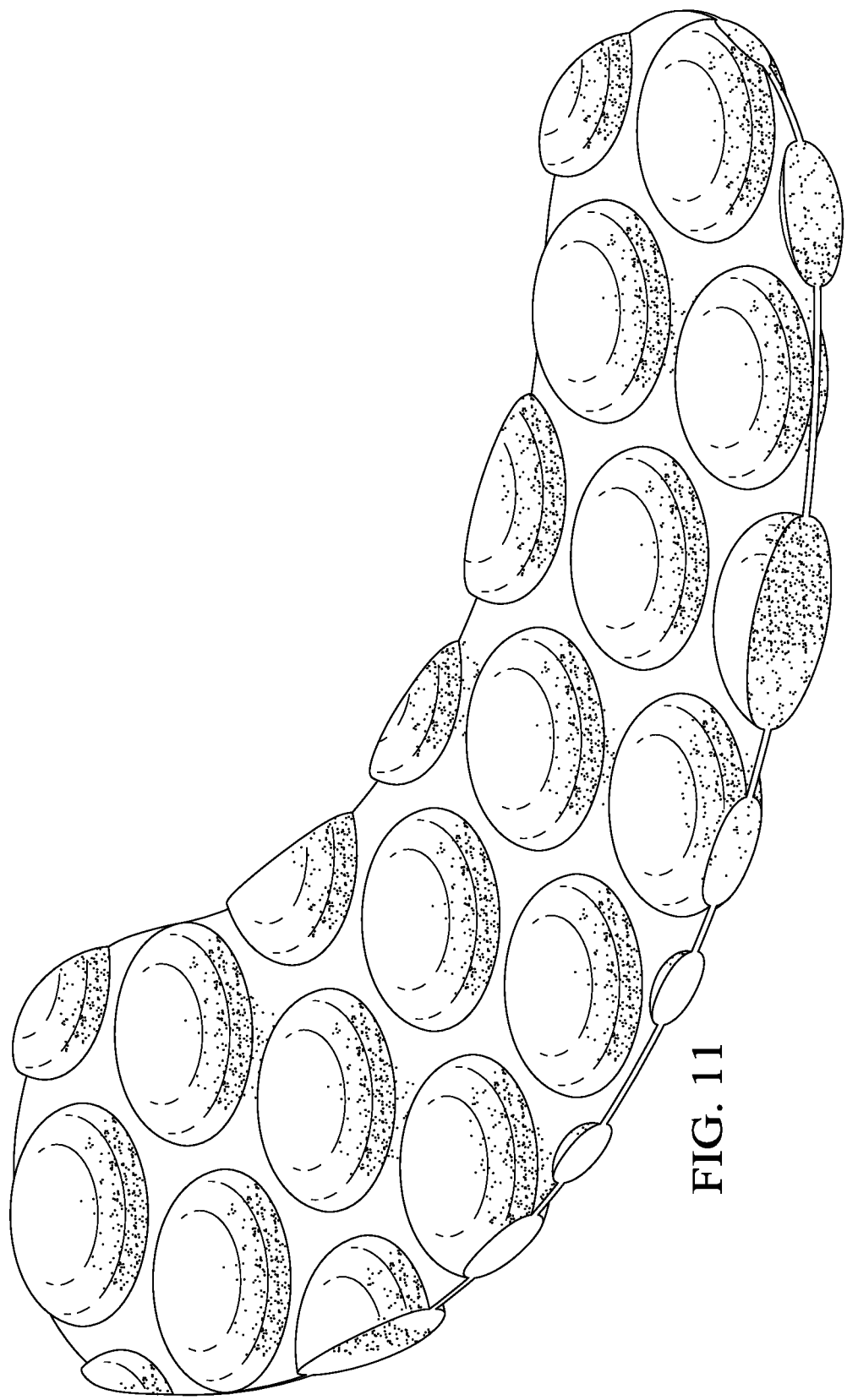
FIG. 11 is a top view of yet another shield having embossing throughout in a pattern so as to leave small circular puffs of un-embossed absorbent material.
Figure 12:
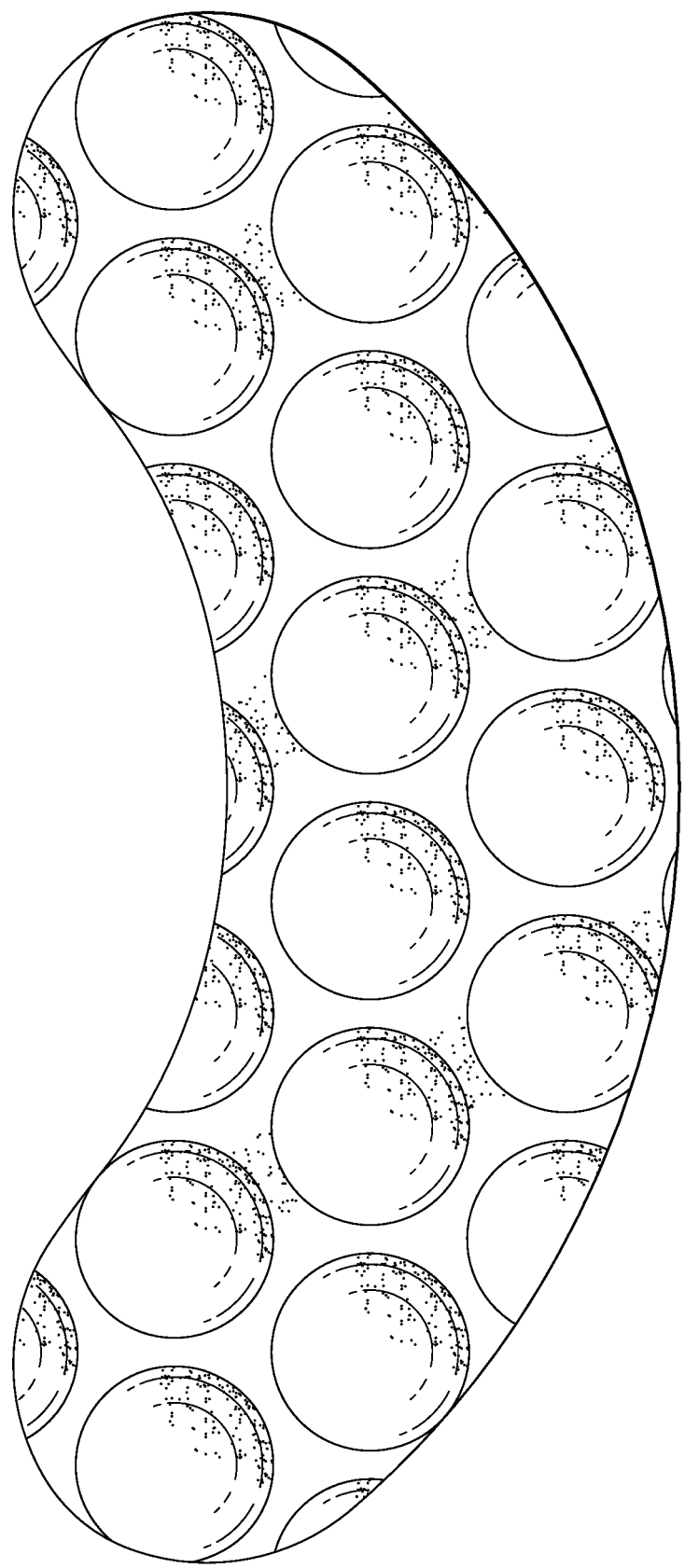
FIG. 12 is a top view of yet another variation of FIG. 11, the shield having embossing throughout in a pattern so as to leave small circular puffs of un-embossed material.
Figure 13:
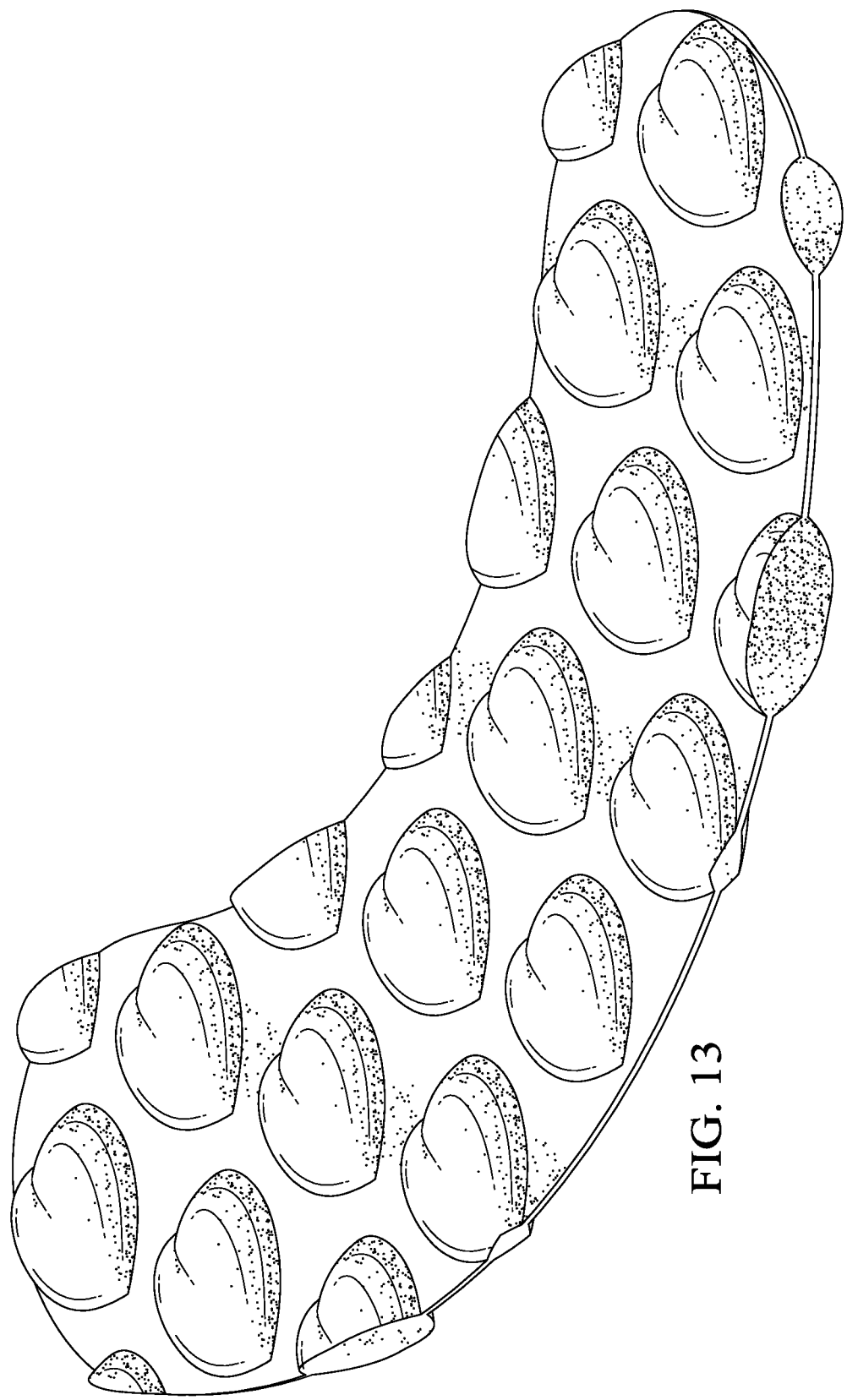
FIG. 13 is a top view of yet another shield having embossing throughout in a pattern so as to leave small heart-shaped puffs of un-embossed material.
Figure 14:
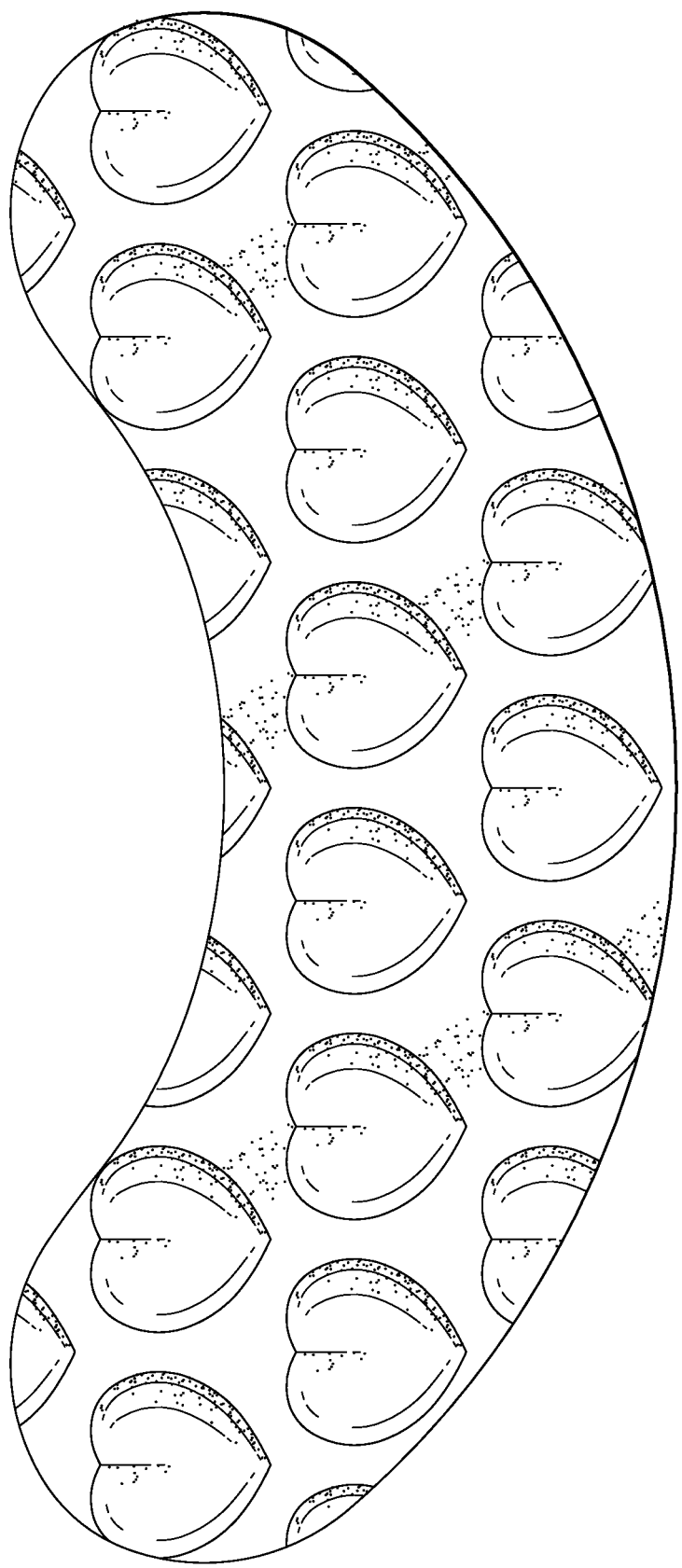
FIG. 14 is a top view of yet another variation of FIG. 13, the shield having embossing throughout in a pattern so as to leave small heart-shaped puffs of un-embossed material.

FIG. 4 shows a variety of shapes that could be used, here each having at least one edge that is convex, and one variation having a tab, for gripping during removal. A simple rectangle would also suffice, but the convex edges, provides a better wrinkle free fit.

FIG. 5-14 show a variety of design and embossment patterns.

Preferred materials are natural fibers that are biodegradable, highly absorbent and non-antigenic or irritating to baby skin. However, synthetics may be preferred as providing superior wicking and airflow properties. The types of materials that can be used are described below:

Bamboo—Bamboo fiber is an incredibly absorbent material and naturally resistant to bacterial growth, making it an excellent fabric for a shield. Bamboo is available in a variety of fabric styles, including terrycloth, velvet, fleece and flannel.

Cotton—Cotton is the most commonly used plant based fiber on earth and cotton is often used in reusable diapers. The cotton outer layer can be woven, such as cotton velvet or terrycloth and a loose cotton fiber can be used as the filling. Terry, velvet and brushed cottons (flannel) may be particularly suitable for use herein. Cottonique® makes a natural unbleached cotton that is pH balanced for skin, and may be a particularly preferred material.

Hemp—Hemp is a natural fiber that is more hydroscopic than cotton and naturally resistant to bacterial growth. Hemp materials are quite thin, while still absorbent, but they do not absorb as quickly as cotton or polyester. For this reason, in diapers, hemp fabric is often paired with another absorbent fiber, such as in a hemp/cotton blend. Hemp is available in a variety of fabric styles, including terrycloth, velvet and flannel.

Modal—Modal fabric is similar to bamboo in that it is made from wood pulp, however it is made from the wood pulp of beech trees rather than bamboo. Modal has an incredibly silky feel to it, and maintains its softness and wears well over time. One key advantage to modal fabrics in diapering is that they are resistant to the mineral build up that many struggle with when washing such materials in hard water.

Polyester—Polyester is a man-made material, and as such is made with chemicals and petroleum. In diapering, the word "polyester" is often replaced with "microfiber," "minky," and occasionally "zorb". These products are quite absorbent, but they do wear out over time, losing the ability to absorb with continued wear. Microfiber is often used in pocket diapers and should never be used directly against a baby's skin as it can be irritating. The microscopic structure of these fibers that makes them so absorbent can also make them incredibly difficult to get thoroughly clean with each washing, and therefore tend to develop odors over time.

Silk—Silk is the only 100% natural wicking material able to help keep baby bottoms drier and is naturally acidic. Silk has natural anti-bacterial properties that may keep yeast and diaper rash at bay. Silk liners are a recommended accessory for cloth diapering. Knit silk liners are also available.

Fleece—Polyester fleece comes in many weights and varieties and can perform several different functions. The thinnest fleece is often used on the interior of a diaper as a stay dry layer, as described further below. Thicker fleeces can be used in making a breathable cover for diapers. If there is a very absorbent diaper underneath, fleece can be an incredibly successful fabric as a cover for diapers since it is so water resistant, yet porous for breathability. It is often sewn into "soakers," "shorties," and "longies" at home for economical and adorable diapering. A double layer fleece shield may be particular beneficial, avoiding the need for any filler, and yet very soft and allowing good airflow.

"Stay Dry" Fabrics—Suedecloth, microfleece, and athletic fabrics—which are porous polyester fabrics—are frequently used in diapering as a "stay dry" layer. These fabrics are not designed to absorb liquids, so when used inside a diaper as the layer closest to a baby's skin the urine passes through them and into the absorbent layers of the diaper. This helps to keep moisture away from a baby's skin longer, helping the skin to "stay dry."

Wool—Wool is the most natural and breathable material available for use in diaper covers. It is naturally resistant to bacterial growth and, when lanolized, it is incredibly water resistant. Wool interlock fabric, as well as knit and crocheted items, all require hand washing and lanolizing but many who use wool as their choice for diaper covers find the benefits of wool to be worth the higher maintenance of the material. One of the benefits of wool is that it is naturally acidic.

Nonwoven Polypropylene and polyethylene liners—These are typically used in disposable diapers against the baby's skin to provide a wicking surface, pulling fluid to the absorbent liner or gel inside the diaper. See e.g., US20110092935 Fabric liner for skin-contacting items.

Many of these materials listed above have already been developed for diaper use, including super heavy bamboo fleece, bamboo heavy fleece, bamboo fleece, cotton sherpa (sherpa is a synthetic knitted fabric, smooth on one side and like sheeps wool fleece on the other), bamboo hemp fleece, hemp fleece, bamboo French terry, bamboo velour, white birdseye mesh wicking, hemp French terry, Polyolefin, absorbent wood based cellulose, and cotton. Each of these have also been tested for bacterial growth by our engineers, and the top three picks were cotton sherpa, bamboo heavy fleece & super heavy bamboo fleece.

Cotton sherpa fleece is 90% cotton and 10% polyester of weight 510 gsm/15 oz per sq. yard and is $11 per yard at Diaper Sewing Supplies (numbers can vary, but this was the fabric actually tested). It makes great fitted diapers and diaper inserts, is very durable, shrinks when washed, and this felting up helps give good absorbency. It is often used in fitted diapers with the fuzzy sherpa side against baby's skin.

Bamboo heavy fleece fabric is $16.00 per yard and is 70% bamboo viscose and 30% organic cotton and weight is 400 gsm/25 oz per yard (numbers can vary, but this is the fabric that was actually tested). It is very popular for diaper inserts—especially for heavy wetters overnight. It is quick to grab and hold moisture and shrinks about 10% when washed, and this felting up helps give it good absorbency. It is typically sewn smooth sides out for inserts and soakers. It is available in Oeko-tex Standard 100—the highest international standard meant for infant items that touch the skin and which certifies that the fibers used in this fabric are free of all known harmful substances.

Bamboo Super Heavy Fleece Fabric is $17.00 per yard and is 70% bamboo viscose and 30% organic cotton of weight: 500 gsm/31 oz per yard (amounts can vary, but this is the fabric that was tested). This fabric is the ultimate in bamboo absorbency, with quick soaking power and lots of capacity. It shrinks when washed and this felting up helps it soak up liquid. It looks and feels just like the other bamboo fleeces but is thicker. It is also available in Oeko-tex Standard 100.

Most preferred the outer layer of the pad is such as to help maintain an acidic pH. Begiun (2010) describes one such material. To achieve a skin-neutral pH value between 4.5 and 5.5 on the surface of adult briefs, they used curled fiber (CMC 525, Weyerhaeuser International Inc., Geneva, Switzerland), a citric acid-crosslinked and a specially processed type of cellulose fiber, interposed between the lining sheet in contact with the skin and innermost superabsorbent polymer (SAP)-containing cellulose fluff. Curled fiber is modified in a citric acidic environment and this favors the formation of cross-links to maintain a twisted and curled fiber architecture. This type of fiber has soft haptics and an excellent ratio between fluid holding and distribution characteristics. Beneath the curled fiber layer the normal cellulose and SAP containing core binds the absorbed fluid and reduces the re-wetting at the level of the skin.

In standard polyacrylate superabsorbent briefs with a conventional design, the surface pH was read at values of 7.08±0.03 when wetted with a salt-containing urine replacement solution. Interposing a fluid acquisition layer containing curled fiber between the top fleece facing the patient's skin and the SAP-containing absorption core the surface pH was buffered to 4.58±0.17.

Another way to reduce the pH of the shield is to soak or spray it with citric acid and/or L-lactide and allow the solution to dry. By contrast, if the infant has an acidic diarrhea, a buffer may be better than an acid to lower pH.

Yet another way is to manufacture a material of known pH. See e.g., US20110021104 pH-adjusting textile containing amphoteric polymer composite nanoparticles.

Medicaments can be included in the shield if provided in dry format, such as powders or materials the bind to or were absorbed by the fibers of the shield. It is noted, however, that some medicaments should not be used except under doctors prescription, such as antifungals and certain antibiotics, and all medicaments should be tested and FDA approved before use. Examples of medicaments that could be included in the shield include the following:

Analgesics such as procaine, xylocaine, carbocaine, pramoxine hydrochloride or the like.

Anti-lipase agents such as esterastin, lipstatin, valilactone, tetrahydrolipstatin, panclicin, ebelactone, ajoene, and combinations thereof and said protease inhibitor is a trypsin-chymotrypsin inhibitor.

Anti-protease agents such as a trypsin-chymotrypsin inhibitor.

Antifungal agents such as benzoic acid, salicylic acid, amphotericin B, miconazole, nystatin, tolnaftate or the like or mixtures or combinations thereof.

pH control agents such as inorganic and organic buffers (pK's from 4 to 6), to control pH to between about 4.5 and about 5.5, such as carbonates, maleates, citrates, adipates, or the like, or mixtures or combinations thereof. Weakly basic anion exchange resins of agarose, dextran, cellulose and polystyrene to sequester or augment neutralization of bile salt/acid and contribute to pH control, or mixtures or combinations thereof.

Anti-inflammatory agents such as antihistamines, corticosteroids, or the like, or mixtures or combinations thereof.

Anti-microbial agents such as eugenol, guaiacol, zephiran chloride, or the like, or mixtures or combinations thereof.

Antibiotic agents such as bacitracin, neomycin sulfate, gentamicin sulfate, erythromycin or the like, or mixtures or combinations thereof.

Vitamins. Vitamin B3 has been shown to inhibit urease, thereby helping to maintain correct pH. Vitamin A has also been included in many diaper rash treatments, but there is no evidence to support its inclusion or exclusion.

Emollients. Lanolin is one of the most physiological emollient constituents currently available, containing many of the lipid groups present in the human stratum corneum and having the advantage of permitting water exchange.

U.S. Pat. No. 6,521,087 describes method of binding medicaments to the fibers in a diaper, but other methods could be used, including merely soaking the shield in a solution of medicament and allowing it to dry, or spraying the surface and allowing it to dry. This simple method is expected to be very useful for naturally absorbent fibers.

The following references are incorporated by reference in their entirety for all purposes.

BEGUIN A., et al., Improving diaper design to address incontinence associated dermatitis, BMC Geriatrics 10:86 (2010).

US20080145443 Diaper rash composition and method.
US20110021104 pH-adjusting textile containing amphoteric polymer composite nanoparticles.
US20110092935 Fabric liner for skin-contacting items.
U.S. Pat. No. 4,892,532 Disposable liquid-absorbing article.
U.S. Pat. No. 4,923,454 Microfiber-containing absorbent structures and absorbent articles.
U.S. Pat. No. 4,935,022 Thin absorbent articles containing gelling agent.
U.S. Pat. No. 6,277,770 Durable, comfortable, air-permeable allergen-barrier fabrics.
U.S. Pat. No. 6,521,087 Method for forming a diaper.
U.S. Pat. No. 6,676,645 Breast-milk absorbent pad.
U.S. Pat. No. 6,780,201 High wet resiliency curly cellulose fibers.
U.S. Pat. No. 7,364,639 Method of producing twisted, curly fibers.

The invention claimed is:

1. An intergluteal shield, comprising an absorbent pad lacking any waterproof layers, said pad having a size and a shape to fit into an intergluteal space of a human, thereby separating the glutes and allowing airflow therebetween, said absorbent pad having an absorbent material covered by a soft fabric exterior, and said fabric having a layer of curly cellulose fiber therein.

2. The intergluteal shield of claim 1, further comprising a tab portion of said intergluteal shield protruding from said intergluteal space and suitable for gripping.

3. The intergluteal shield of claim 1, comprising cotton sherpa fleece or bamboo fleece.

4. The intergluteal shield of claim 1, wherein said absorbent pad has an acidic pH.

5. The intergluteal shield of claim 1, said absorbent pad having a pH of 4.5-5.

6. The intergluteal shield of claim 1, wherein said shape is a heart shape, a crescent shape, a rectangular shape, or a shape having a convex curve on an edge thereof.

7. The intergluteal shield of claim 1, wherein said absorbent pad comprises a dried buffer having a pKa of 4.5-5.5.

8. The intergluteal shield of claim 1, wherein said absorbent pad comprises a dried medicament for the treatment of diaper rash.

9. The intergluteal shield of claim 1, wherein said absorbent pad is selected from bamboo, cotton, hemp, silk or lanolized wool fleece or combinations thereof.

10. The intergluteal shield of claim 1, said fabric being a non-woven stay dry fabric.

11. The intergluteal shield of claim 1, said fabric being a non-woven stay dry fabric comprising a non-woven polypropylene and polyethylene material.

12. The intergluteal shield of claim 1, wherein said fabric is a terrycloth or velvet or flannel having a pile, wherein said pile is oriented to the outside of said pad.

13. An intergluteal shield, comprising an absorbent pad lacking any waterproof layers, said pad having a size and a shape to fit into an intergluteal space of a human, thereby separating the glutes and allowing airflow therebetween, further comprising a tab portion of said intergluteal shield protruding from said intergluteal space and suitable for gripping, said tab portion being less than 3 square inches, said absorbent pad having an absorbent material covered by a soft fabric exterior, and said fabric having a layer of curly cellulose fiber therein.

14. An intergluteal shield, comprising an absorbent pad of pH 4.5-5 and lacking any waterproof layers, said pad having a size and a shape to fit into an intergluteal space of a human, thereby separating the glutes and allowing airflow therebetween, said absorbent pad having an absorbent material covered by a soft fabric exterior, and said fabric having a layer of curly cellulose fiber therein.

* * * * *